(12) United States Patent
Rio

(10) Patent No.: US 6,749,341 B2
(45) Date of Patent: Jun. 15, 2004

(54) BALL BEARING

(75) Inventor: Eddy Del Rio, Royal Palm Beach, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 43 days.

(21) Appl. No.: 10/153,368

(22) Filed: May 22, 2002

(65) Prior Publication Data

US 2003/0219184 A1 Nov. 27, 2003

(51) Int. Cl.$^7$ ............................................... F16C 33/40
(52) U.S. Cl. ...................... 384/528; 384/490; 384/512; 384/523
(58) Field of Search ................................. 384/445, 456, 384/490, 512, 513, 516, 523, 528, 529, 530, 531, 532, 533, 534

(56) References Cited

U.S. PATENT DOCUMENTS

| | | | |
|---|---|---|---|
| 1,976,637 A | * | 10/1934 | Scott ........................... 384/528 |
| 3,043,634 A | | 7/1962 | Coley |
| 3,271,087 A | | 9/1966 | Wieland et al. |
| 3,514,166 A | | 5/1970 | Coley |
| 5,156,462 A | * | 10/1992 | Jacob et al. ................... 384/49 |

FOREIGN PATENT DOCUMENTS

| | | |
|---|---|---|
| DE | 201 04 813 U1 | 8/2001 |
| GB | 2 107 003 A | 4/1983 |

* cited by examiner

Primary Examiner—Thomas R. Hannon
(74) Attorney, Agent, or Firm—Norman Friedland

(57) ABSTRACT

A ball bearing construction including a plurality of balls supported in a cage and each ball within a row is off-set relative to each other. In certain applications the rolling surface of the balls bear against the rotating shaft and the case enclosing the bearing. The number of balls and the number of rows are predicated on the particular application. This invention is particularly efficacious for use for medical instruments. In other embodiments an inner race and/or outer race can be utilized with this configured balls and cage.

18 Claims, 5 Drawing Sheets

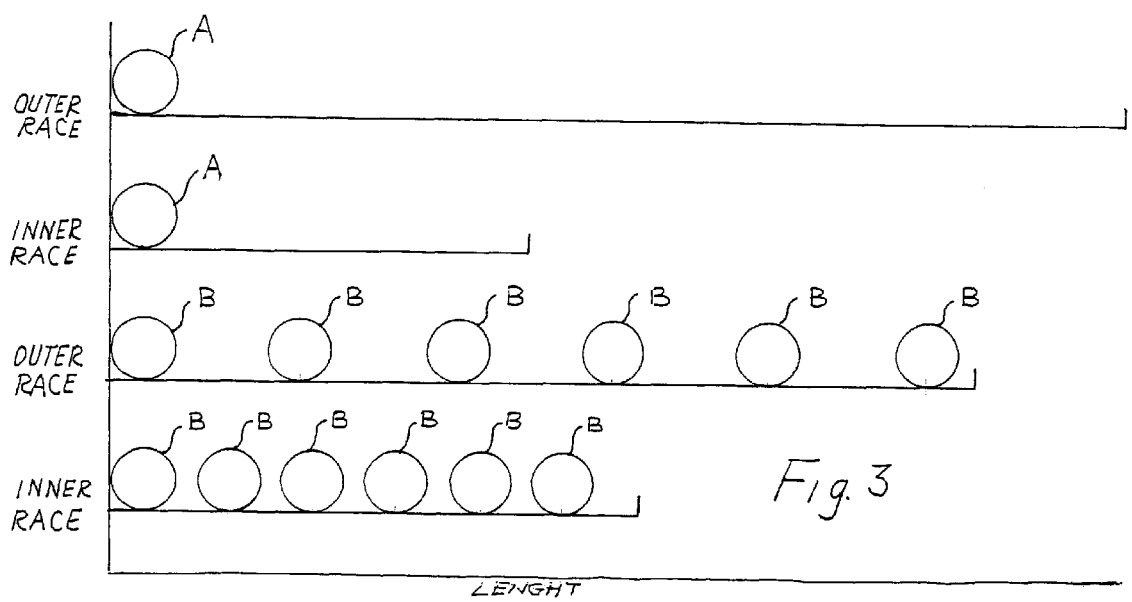
Fig. 3
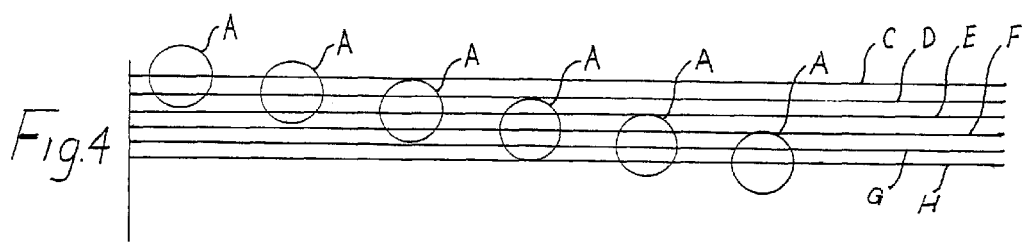
Fig. 4
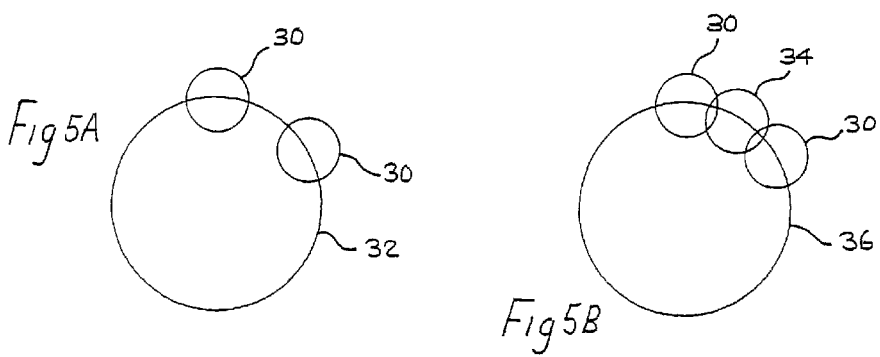
Fig 5A
Fig 5B

BALL BEARING

TECHNICAL FIELD

This invention relates to bearings for supporting rotary members and more particular to ball bearings.

BACKGROUND OF THE INVENTION

As is well known in this technology, there are sundry ball bearings for supporting rotating shafts and the like and are characteristic of typically transmitting loads and supporting axial or thrusts loads and often employed for carrying heavy radial loads. Typically, the balls of a ball bearing configuration is supported between a pair of concentric rings, an inner race and an outer race and the balls lie in a plane normal to the axis of rotation. Also, particularly in high speed operation, the races are pre-loaded so as to keep the balls in radial alignment. Obviously, as is well known to those skilled in the art, in these types of bearings, whether it be the single or double row ball bearings configuration, a misalignment of the balls relative to each other would cause the misaligned ball to rotate faster than the other balls, creating heat and friction, resulting in failure or premature wear of the bearing.

I have found that I can obtain an improved ball bearing by judiciously orienting the balls in the bearings so that the circumferential path of the balls is somewhat in the shape of a helical path. In this arrangement each of the balls follow an independent path alleviating the wear that would otherwise occur in the heretofore known ball bearing. The balls are supported in a cage and can be assembled with or without the inner race and/or outer race and do not require pre-loading. When assembled without the races, the ball for a given envelope is larger which is another feature that serves to enhance the wear characteristics of the bearing.

In many medical instrument applications, the ball bearings typically are utilized for radial loads inasmuch as the supporting mechanism typically requires the assembly and disassembly of the shaft or the like that is supported by the bearings. For example, in drills utilized in surgical operations the cutters are driven by a motor and the cutters are typically changed for different sizes and types. The Anspach Company, the assignee of this patent application, for instance, manufactures and sells the EMax™ drill that is utilized with different sized and shaped cutters which cutters are slidably mounted into the drill.

Another example of the bearings utilized for surgical instruments is disclosed and claimed in U.S. patent application Ser. No. 09/962,989 filed on Sep. 25, 2001 entitled "Bearings For Surgical Instruments" and assigned to the same assignee as this patent application, which is incorporated herein by reference. This patent application is being cited here because in one embodiment, this invention replaces one of the bearings in the Micro Dissection Attachment (MDA) disclosed in this patent application. As taught in the aforementioned patent application, the MDA utilizes journal bearings made from a polymer of polyimide resin and graphite composition and is judiciously configured so that there are two points of contact of the mating surfaces. This bearing configuration allows for the miniaturizing of the MDA at the distal end so as to enhance the line of vision of the cutter for the surgeon to facilitate the procedure in surgery. The journal bearing of this teachings also enhances the wear characteristics of the MDA. Like the journal bearing as taught in the U.S. patent application Ser. No. 09/962,989, supra, the ball bearing of this invention can be made sufficiently small so that it affords the characteristics of having a line of sight for the surgeon doing a surgical procedure similar to the characteristics that is sought after in the MDA application, while enhancing the load characteristics of the instrument. Additionally, while the present ball bearing of this invention affords a significantly miniaturized bearing wherein the diameter of the balls are in the order of 0.032 inch, for example, there is no limitation in the upper end of ball size of the bearing. Hence, for surgical instruments where the ball bearings only support radial loads, it is fundamentally important that the bearings sizes are small and factually, the smaller the bearing the better.

The bearing made in accordance with this invention affords the following characteristics although other characteristics may be realized:

1) The ball bearings when utilized without the races are larger in diameter and hence, enhance the wear characteristics of the bearing;
2) The balls do not roll on common tracts and hence, each ball runs on an independent track which enhances the wear characteristics of the bearing,
3) The bearing can be miniaturized so as to maintain a small diameter of the envelope;
4) the bearings are characterized as easy to manufacture, less expensive than heretofore known bearings, are maintenance free and are reliable and have a long operational life;
5) the material of the bearings can be any well known material, be it ceramic or metal;
6) pre-loading is not necessary;
7) the assembly and disassembly of the bearing are simplified in comparison to heretofore known ball bearings; and
8) misalignment of the balls is obviated.

SUMMARY OF THE INVENTION

An object of this invention is to provide an improved ball bearing.

A feature of this invention is that the balls are discretely off-set so that each ball lies in a different plane transverse to the rotating axis. There are no limits on the number or rows of balls that can be included in a single bearing and the number of rows and balls in each row are predicated on the particular design.

Another feature of this invention in certain embodiments, no races are utilized. In other embodiments the ball bearing can be constructed with or without the inner race and/or the outer race.

This invention is characteristic of enhancing the life of the bearing, adaptable for high speed operation, miniaturization for reducing the envelope size of the bearing chamber, low maintenance costs, and easy to assemble and disassemble.

The foregoing and other features of the present invention will become more apparent from the following description and accompanying drawings.

BRIEF DESCRIPTION OF THE DRAWINGS

These figures merely serve to further clarify and illustrate the present invention and are not intended to limit the scope thereof.

FIG. 3 is a graphical illustration comparing the inner and outer races of this invention with the prior art plotted against length of travel of the ball;

FIG. 4 is a projected view in schematic illustrating the travel pattern of the balls of the ball bearing of this invention;

FIG. 5A is a schematic illustration of the ball bearing configuration of this invention where two rolls of balls are utilized.

FIG. 5B is a schematic illustration of the ball bearing configuration of this invention where two rolls of balls are utilized.

DETAILED DESCRIPTION OF THE INVENTION

This invention is described in its preferred embodiment showing the details of the ball bearing of this invention and as one skilled in the art will appreciate, the ball bearing of this invention has a wide variety of applications and is not limited to any particular application. As one skilled in this art will appreciate since the balls of the ball bearing of the present invention can be miniaturized this invention is particularly efficacious in the medical instrument field.

Figure 2:
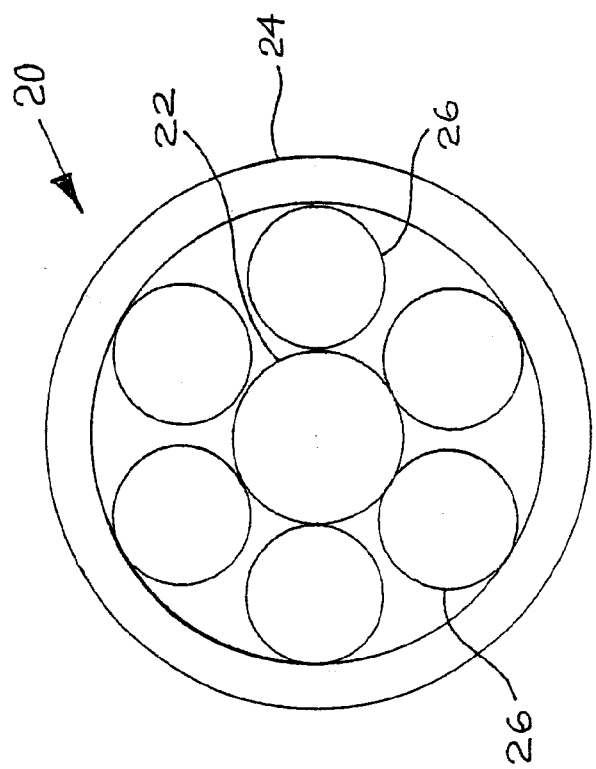
FIG. 2 is an end view in elevation of the ball bearing of this invention mounted to support a rotary shaft.
Figure 1:
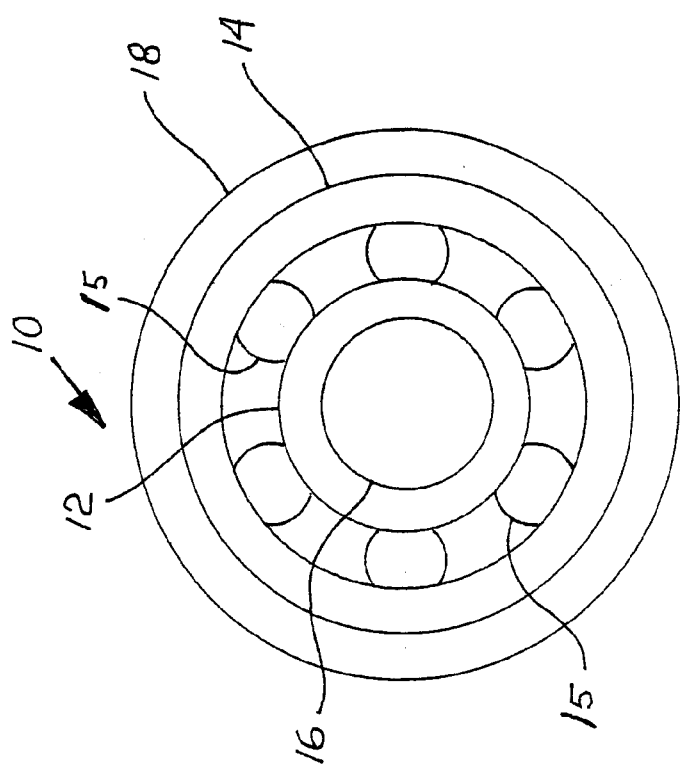
FIG. 1 is a end view in elevation of a prior art ball bearing mounted to support a rotary shaft.

Referring now to FIGS. 1 and 2 which schematically compares the ball bearing construction of a prior art ball bearing illustrated by reference numeral 10 having an inner race 12 and an outer race 14 and a plurality of spherical balls 15 circumferentially spaced there-betweeen for supporting shaft 16 within the sleeve-like housing 18 and the ball bearing of this invention generally illustrated by reference numeral 20 that includes shaft 22 and the sleeve-like housing 24 and a plurality of spherically shaped balls circumferentially spaced there-between. As can be seen from these figures, the prior art ball bearing 10 includes an inner and outer race, while the ball bearing 20 of this invention does not. What is apparent from this comparison is that the balls in the ball bearing of the present invention (FIG. 2) are significantly larger than the balls in the prior art configuration (FIG. 1). The larger ball configuration affords a lower spin rate of each of the balls and larger wearing surface, the consequence of both parameters resulting in improved wear characteristics and hence, a longer life of the bearing.

In addition, as can be seen in the graph of FIG. 3, viewing ball A in relation to the outer race, which represents one of the balls in the ball bearing of this invention travels over a single track while the six balls B of the prior art six balls ball bearing travel over a single track. Obviously, since each of the balls of the ball bearing of the present invention are displaced laterally or offset with respect to each other, each of the six balls travel over a complementary and independent track.

Looking at the outer race in a comparison of the prior art ball bearing and the present invention, again, the six balls travel over a single track compared to a single ball traveling over a single track. Even though the track of the prior art ball bearing is longer, the number of balls in the prior art configuration traveling over the same distance is much greater than the travel distance in the present invention.

Hence, in accordance with this invention, each of the balls 26 are off-set relative to each other. This is best seen in FIG. 4 where the balls A are shown to be off-set and each ball is displaced laterally relative to each other such that each ball lies parallel plane passing through the axial center or rotating axis of the bearing. Hence, each ball rolls over its own track as represented by the lines C, D, E, F, G, and H. Again, because there is less wear in a single given track when comparing the ball bearing of the present invention to the ball bearing of the prior art, the life of the bearing made in accordance with this invention is enhanced.

Ball bearings 20 can be made from metallic or non-metallic material. Obviously, if non-metallic material is utilized, the unit is not affected by magnets or electromagnets and the like.

FIG. 5 is a schematic illustration of another embodiment of this invention. In certain applications utilizing the prior art ball bearings, it is desirable to utilize a pair of ball bearings mounted side-to-side. Obviously, in this arrangement axial alignment of the balls in each ball bearing can either be in coincidence with the axial alignment or can be displaced from the axial alignment, and this occurrence is happenstance, i.e. the relationship of the balls in one of the ball bearings has no bearing on the relationship of the balls in the other ball bearing, namely, the balls merely can seek its own position. On the other hand and in accordance with the present invention, the balls which are held by a single cage as will be described in more detail hereinbelow can be axially offset or displaced. This is best seen in FIG. 5A, which is a schematic illustration of this invention where the balls 30 in a single row of balls in a ball bearing of this invention are retained by the cage schematically illustrated by the circle 32. When a second row of balls as illustrated in FIG. 5B are added the two balls 30 are circumferentially displaced in a single offset row of balls and the single ball 34 is essentially oriented, as seen from an axial view, between the two balls 30, or stated another way the balls in the first row are radially off-set from the ball 34 in the second row of balls. If one were to draw a straight line axially through the center of the balls in the first row of balls, that line would not be in coincidence with the balls in the second row. The cage 36, in this instance, will be longer to accommodate the second row of balls. This arrangement, not only enhances the distribution of the radial loads as compared with the two rows of balls by mounting two prior art ball bearings side-by-side, but also enhances the structural integrity of the ball bearing because the single bearing acts over the increased length of the envelope of the bearing cavity and hence, the two rows of balls work in unison with each other.

Figure 6:
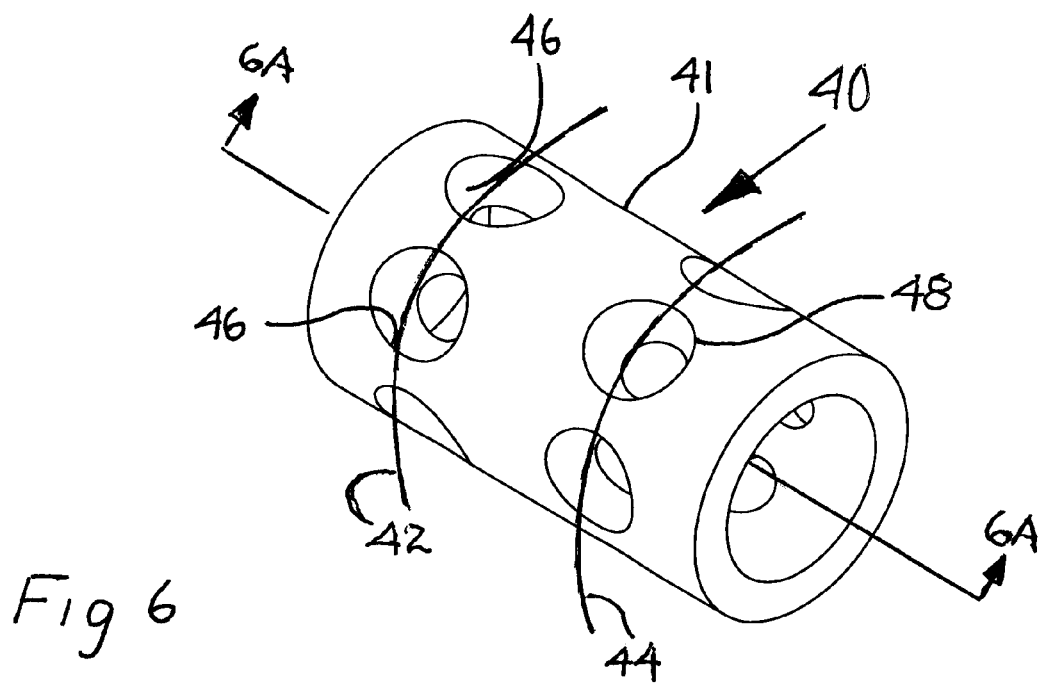
FIG. 6 is a perspective view of the cage for two rolls of balls utilized in this invention.
Figure 7:
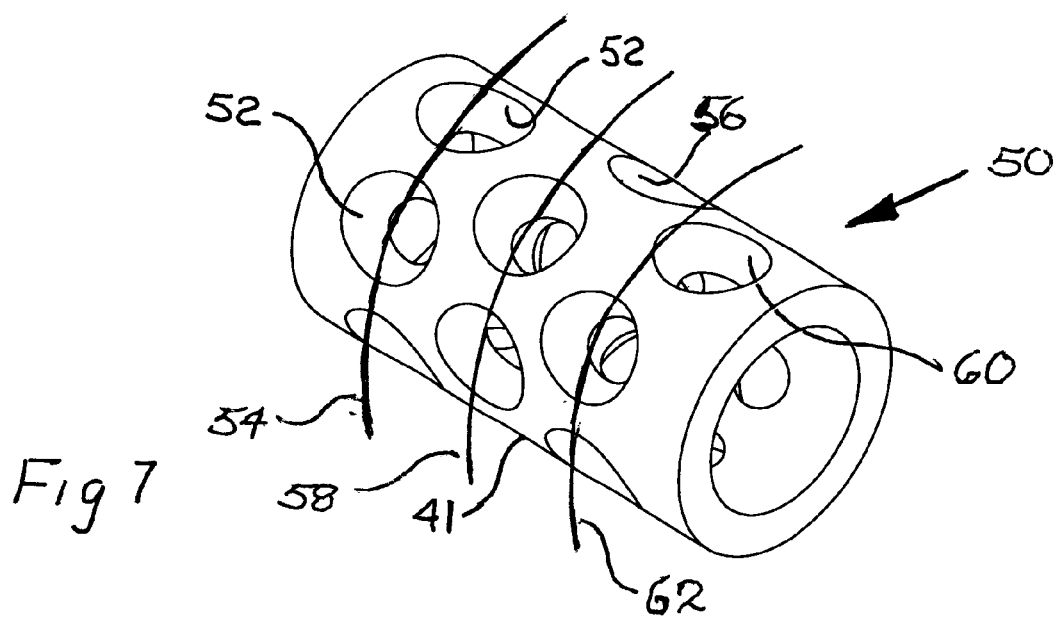
FIG. 7 is a perspective view of a three row cage exemplifying an embodiment of one construction of this invention.
Figure 6A:
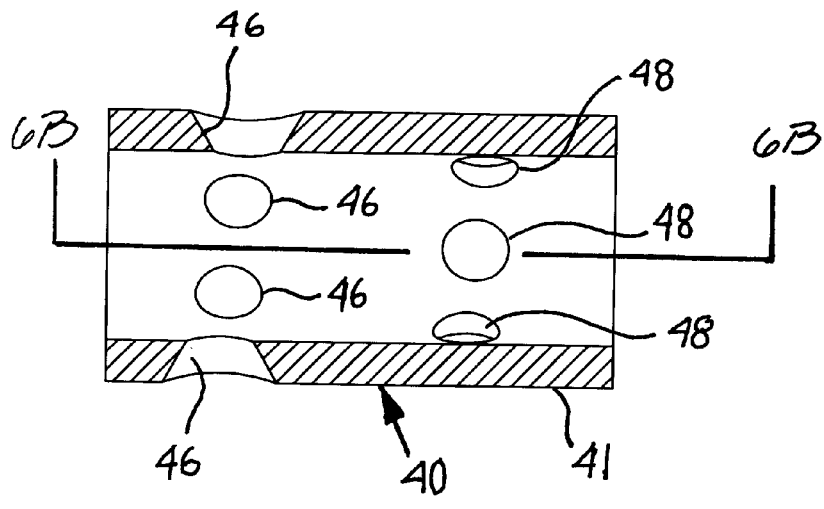
FIG. 6A is a sectional view taken along the lines 6A—6A of FIG. 6.
Figure 6B:
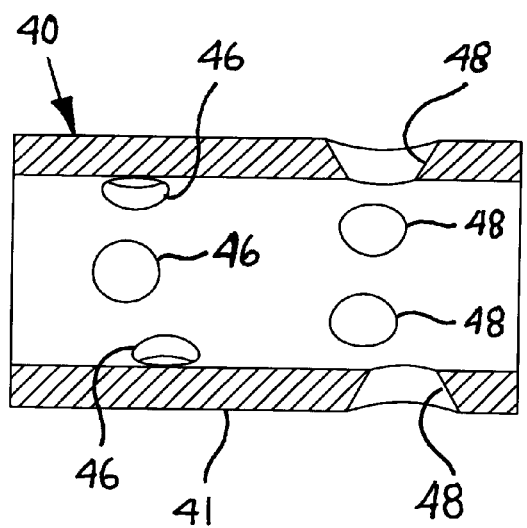
FIG. 6B is a sectional view taken along the lines 6B—6B of FIG. 6A.

FIGS. 6 and 7 illustrate the cages of the ball bearing of this invention, where the cage 40 shown in FIG. 6 is for a two row ball configuration and the cage 50 shown in FIG. 7 is for a three row ball configuration. As can be seen in FIG. 6, the two row ball cage 40 is a cylindrical hollow main body portion or sleeve-like member 41 has two rows 42 and 44 of circumferentially spaced conically shaped holes 46 and 48 discretely located in a helical path. Each of the plurality of holes 46 and 48 serve to hold a single spherical ball 26 (FIG. 1) so that a portion of the ball protrudes beyond the lower portion of the conically shaped hole and the upper portion of the ball 26 protrudes through the top portion of the conically shaped hole, that is to say the diameter of the upper portion of the hole is larger than the diameter of the ball bearing 26 and the diameter of the lower portion of the countersunk hole is smaller than the diameter of the ball bearing 26. The cage 50 for supporting three rows of balls as shown in FIG. 7 is similarly constructed, namely, the holes 52 in row 54, the holes 56 in row 58 and the holes 60 in row 62 are all conically shaped and the same dimension with the larger diameter thereof adjacent the outer surface and each row of holes is oriented to follow a helical path so as to off set the balls when assembled.

It is apparent from the foregoing that ball bearings made in accordance with this invention require a smaller envelope size for the bearing cavity when one or the other race is not utilized and that in this type of configuration the ball is larger in comparison with the same outer diameter bearing of the prior art construction so as to have a larger contact surface with the mating components in contact with the ball. Because the balls are offset in this invention each ball rides on its own track and hence, the wear of the bearing is enhanced. In addition, particularly in a two, three or multiple rows of balls the load carrying capabilities of the bearing is increased allowing a smaller bearing to be utilized as compared to the heretofore known ball bearings.

Figure 8:
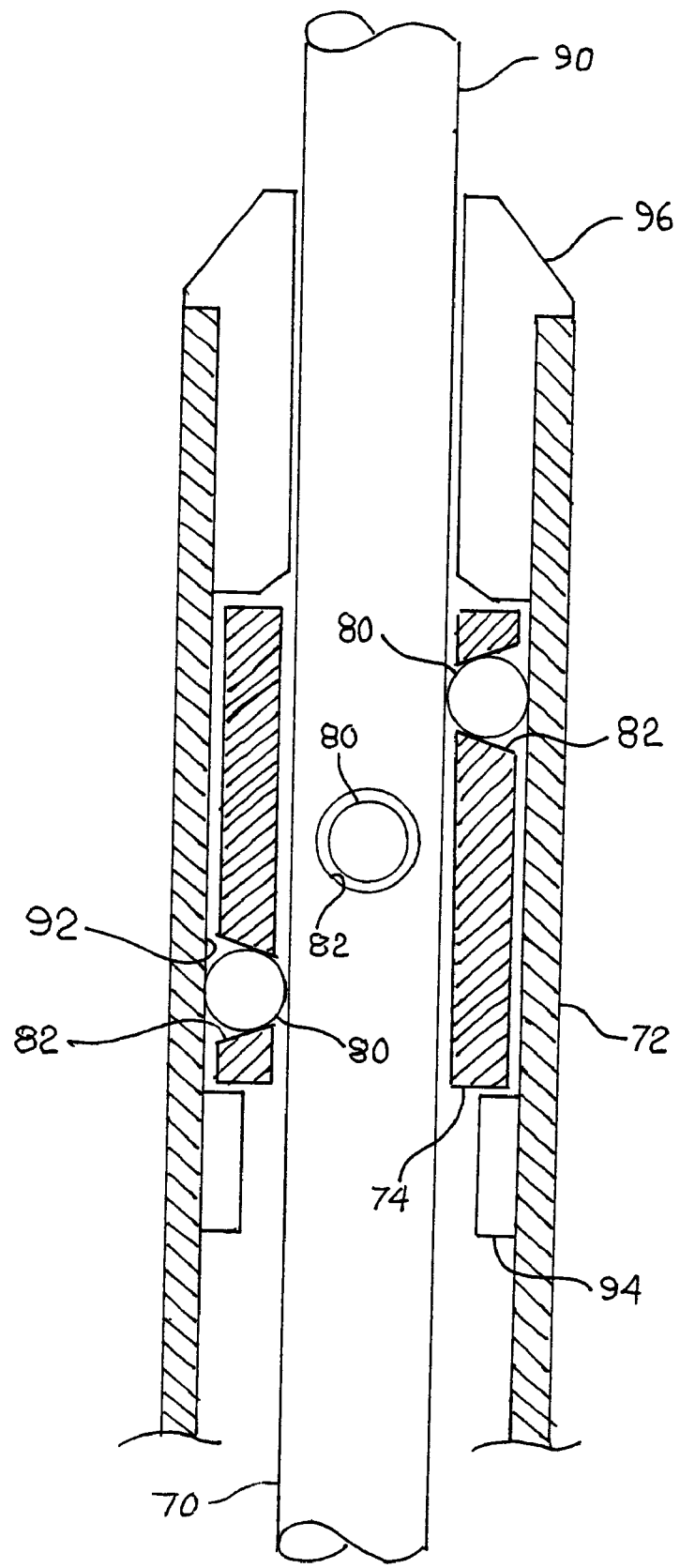
FIG. 8 is a sectional view showing the details of a two row ball bearing configuration of the bearing configuration of this invention.

As mentioned in the above paragraphs, the ball bearing made in accordance with this invention is extremely efficacious for medical instrument applications because the balls can be made extremely small, say 32 thousands of an inch (0.032) plus or minus 0.005 inch. Also, as mentioned in the above paragraph, the ball bearing of this invention is easy to assemble. In the prior art ball bearings that include an inner race and an outer race, the dimensions are critical so that the units are press fitted onto the surface of the mating chamber and the shaft and the balls must be perfectly aligned relative to each other and the shaft. In the present invention, there is no interference fit or the like and the balls roll onto the shaft and into the tube or sleeve that defines the bearing chamber facilitating the assembly and disassembly thereof This is best illustrated in FIG. 8 which merely illustrates an exemplar way in which the bearings can be mounted and used. For example, the rotary shaft 70 may be the shaft of a cutter supported in a tube 72 by the ball bearing 74 made in accordance with this invention. This illustration contains three rows X, Y, and Z and each row carries six (6) spherical balls 80 retained in conically shaped holes 82 formed in cage 84. It will be appreciated that the rolling surfaces of the balls 80 bear directly against the outer surface 90 of shaft 70 and the inner surface 92 of the tube 72; there being no inner race nor outer race. In this example the diameter of the shaft 70 is substantially 0.093 inch, the outer and inner diameters of the sleeve 72 are 0.237 inch and 0.187 inch, respectively and the balls are substantially 0.031 inch. These, dimension are obviously very small and hence, the bearing 74 is miniaturized. Assembling this unit when each component is disassembled entails sliding the cage on the shaft 70, (if the shaft is not adaptable of being used a cylindrical fixture would serve the same purpose and would be removed once the bearing is in place) applying a small amount of light commercially available grease so that a small amount migrates into each of the holes 82, mounting the balls 80 into each of the holes 82, (they being so small may require the use of tweezers to manipulate the balls) sliding the cage into the tube 72 (by virtue of the grease, the balls will remain in its respective hole), which is a simple matter since the balls roll on the respective surfaces. And, then securing the ball bearing 74 into place by providing a shoulder 94 at one end and a nose piece 96 at the other end to bear against the respective ends of the cage. The nose piece is force fitted into the end of tube 70 so that it does not allow the bearing to become dislodged.

While the details of this invention was described in connection with a ball bearing assembly that didn't include an inner race and an outer race, as one skilled in this art will appreciate the teachings of this invention can be applied to a ball bearing construction that includes either an inner race or an outer race or both. Obviously, in applications where it is desirable or required to maintain a miniaturized or small outer diameter, the ball bearing of this invention will be constructed without either the inner race and outer race.

Although this invention has been shown and described with respect to detailed embodiments thereof, it will be appreciated and understood by those skilled in the art that various changes in form and detail thereof may be made without departing from the spirit and scope of the claimed invention.

What is claimed is:

1. A ball bearing construction for supporting a rotating shaft, said ball bearing construction including a cage having a plurality of holes arranged to be offset from each other and each of a plurality of spherically shaped balls mounted in each of said plurality of holes, each of said spherically shaped balls of said plurality of spherically shaped balls include an upper rolling surface and a lower rolling surface wherein said upper rolling surface of each of said spherically shaped balls of said plurality of spherically shaped balls extends above the upper surface of said cage and said lower rolling surface of each of said spherically shaped balls extends below the lower surface of said cage for engaging said rotating shaft.

2. A ball bearing construction as claimed in claim 1 wherein said plurality of holes are circumferentially spaced and are oriented to define a helical pattern.

3. A ball bearing construction as claimed in claim 2 wherein each of said holes are conically shaped and extend through the cage wherein the larger opening of said conically shaped hole is larger than the diameter of each of said spherically shaped balls and the smaller opening of said conically shaped hole is smaller than the diameter of each of said spherically shaped balls.

4. A ball bearing construction as claimed in claim 3 wherein the larger diameter of said conically shaped hole is on the outer surface of said cage and the smaller diameter of said conically shaped hole is on the inner surface of said cage.

5. A ball bearing construction for supporting a rotating shaft, said ball bearing construction including a cage having a sleeve-like main body, said main body having an upper cylindrically shaped surface and an inner cylindrically shaped surface concentric to said upper cylindrically shaped surface, a plurality of circumferentially spaced holes formed in said main body and extending therethrough, and each of said plurality of circumferentially spaced holes being off-set from each other and oriented to define a substantially helical path, and each of a plurality of spherical balls mounted in each said holes and being retained thereby, each of said plurality of spherical balls having an upper rolling surface and a lower rolling surface whereby said upper rolling surface extends beyond the upper cylindrically shaped surface of said main body and said lower rolling surface extends beyond said inner cylindrically shaped surface for rotary supporting said rotating shaft.

6. A ball bearing construction as claimed in claim 5 wherein each of said circumferentially spaced holes are conically shaped where the larger diameter is on the upper cylindrically shaped surface and the smaller diameter is on the lower cylindrically shaped surface.

7. A ball bearing construction as claimed in claim 5 wherein said plurality of circumferentially spaced holes defines a first row, a second row of plurality of circumferentially spaced holes formed in said main body and axially spaced from said first row and being off-set from each other and oriented to define a substantially helical path, and each of plurality of additional spherical balls mounted in each said circumferentially spaced holes of said second row and being retained thereby, each of said plurality of additional spherical balls having an upper rolling surface and a lower rolling surface whereby said upper rolling surface extends beyond the upper cylindrically shaped surface of said main body and said lower rolling surface extends beyond said inner cylindrically shaped surface and said second row of holes being equal in number and dimension of said first row of holes.

8. A ball bearing construction as claimed in claim 7 wherein the plurality of circumferentially spaced holes in said first row is radially offset from the plurality of circumferentially spaced holes in said second row of circumferentially spaced holes.

9. A ball bearing construction as claimed in claim 7, including a third row of plurality of circumferentially spaced holes formed in said main body and axially spaced from said first row and said second row and being off-set from each other and oriented to define a substantially helical path, and each of plurality of another additional spherical balls mounted in each said circumferentially spaced holes of said third row and being retained thereby, each of said plurality of another additional spherical balls having an upper rolling surface and a lower rolling surface whereby said upper rolling surface extends beyond the upper cylindrically shaped surface of said main body and said lower rolling surface extends beyond said inner cylindrically shaped surface and said second row of holes being equal in number and dimension of said first row of holes.

10. A ball bearing construction as claimed in claim 9 wherein the plurality of circumferentially spaced holes in said second row is radially offset from the plurality of circumferentially spaced holes in said third row of circumferentially spaced holes.

11. In combination, a rotary shaft, a tube surrounding said rotary shaft and radially spaced therefrom, a ball bearing mounted in said space, said ball bearing including a cage having a plurality of holes arranged to be offset from each other and each of a plurality of spherically shaped balls mounted in each of said plurality of holes, each of said spherically shaped bails of said plurality of spherically shaped balls include an upper rolling surface and a lower rolling surface wherein said upper rolling surface of each of said spherically shaped balls of said plurality of spherically shaped balls extends above the upper surface of said cage and said lower rolling surface of each of said spherically shaped balls extends below the lower surface of said cage, said upper rolling surface in contact with the inner surface of said tube and said lower rolling surface in contact with the outer surface of said shaft.

12. The combination as claimed in claim 11 wherein said plurality of holes are circumferentially spaced and are oriented to define a substantial helical pattern.

13. The combination as claimed in claim 12 wherein each of said holes are conically shaped and extend through the cage wherein the larger opening of said conically shaped hole is larger than the diameter of each of said spherically shaped balls and the smaller opening of said conically shaped hole is smaller than the diameter of each of said spherically shaped balls.

14. The combination as claimed in claim 13 wherein the larger diameter of said conically shaped hole is on the outer surface of said cage and the smaller diameter of said conically shaped hole is on the inner surface of said cage.

15. A ball bearing for supporting a rotary shaft to a tubular member, said ball bearing mounted in an annular space between said rotary shaft and said tubular member, said ball bearing including a cage having a sleeve-like main body, said main body having an upper cylindrically shaped surface and an inner cylindrically shaped surface concentric to said upper cylindrically shaped surface, a plurality of rows of a plurality of circumferentially spaced holes formed in said main body and extending therethrough, and each of said plurality of circumferentially spaced holes in each of said plurality of rows being off-set from each other and oriented to define a substantially helical path, and each of a plurality of spherical balls mounted in each said holes and being retained thereby, each of said plurality of spherical balls having an upper rolling surface and a lower rolling surface whereby said upper rolling surface extends beyond the upper cylindrically shaped surface of said main body and said lower rolling surface extends beyond said inner cylindrically shaped surface of said main body and said upper rolling surface bearing against said tubular member and said inner rolling surface bearing against said shaft.

16. A ball bearing as claimed in claim 15 wherein each of said circumferentially spaced holes in each of said plurality of rows are conically shaped where the larger diameter is on the upper cylindrically shaped surface and the smaller diameter is on the lower cylindrically shaped surface.

17. A ball bearing as claimed in claim 16 wherein each of said plurality of circumferentially spaced holes in at least one of said rows is radially off set from a plurality of circumferentially spaced holes from another row formed in said main body and axially spaced from said first row and being off-set from each other and oriented to define a substantially helical path, and each of a plurality of additional spherical balls mounted in each said circumferentially spaced holes of said plurality of rows and being retained thereby, each of said plurality of additional spherical balls having an upper rolling surface and a lower rolling surface whereby said upper rolling surface extends beyond the upper cylindrically shaped surface of said main body and said lower rolling surface extends beyond said inner cylindrically shaped surface and said second row of holes being equal in number and dimension of said first row of holes and said.

18. A ball bearing as claimed in claim 17 wherein the plurality of circumferentially spaced holes in said row is radially offset from the plurality of circumferentially spaced holes in said other row of circumferentially spaced holes.

* * * * *